(12) United States Patent
Wang et al.

(10) Patent No.: US 11,793,715 B2
(45) Date of Patent: Oct. 24, 2023

(54) HOT PLASMA DISEASE TREATMENT SYSTEM AND METHOD OF USE THEREOF

(71) Applicant: YANTAI HEALING TECHNOLOGY CO., LTD., Shandong (CN)

(72) Inventors: Yupeng Wang, Shandong (CN); Yi Li, Shandong (CN)

(73) Assignee: YANTAI HEALING TECHNOLOGY CO., LTD., Shandong (CN)

( * ) Notice: Subject to any disclaimer, the term of this patent is extended or adjusted under 35 U.S.C. 154(b) by 1396 days.

(21) Appl. No.: 16/097,612

(22) PCT Filed: Apr. 26, 2017

(86) PCT No.: PCT/CN2017/081966
§ 371 (c)(1),
(2) Date: Oct. 29, 2018

(87) PCT Pub. No.: WO2017/186115
PCT Pub. Date: Nov. 2, 2017

(65) Prior Publication Data
US 2020/0085683 A1     Mar. 19, 2020

(30) Foreign Application Priority Data

Apr. 27, 2016   (CN) .................. 201610272363.X

(51) Int. Cl.
| | |
|---|---|
| *A61B 18/04* | (2006.01) |
| *A61H 33/14* | (2006.01) |
| *A61L 2/00* | (2006.01) |
| *A61N 1/44* | (2006.01) |
| *A61F 7/00* | (2006.01) |
| *A61N 1/02* | (2006.01) |
| *A61N 1/08* | (2006.01) |

(52) U.S. Cl.
CPC .......... *A61H 33/14* (2013.01); *A61B 18/042* (2013.01); *A61F 7/0053* (2013.01); *A61F 7/0085* (2013.01); *A61L 2/0011* (2013.01); *A61N 1/025* (2013.01); *A61N 1/08* (2013.01); *A61N 1/44* (2013.01); *A61F 2007/0093* (2013.01); *A61H 2033/141* (2013.01); *A61H 2230/04* (2013.01); *A61H 2230/207* (2013.01); *A61H 2230/30* (2013.01); *A61L 2/0094* (2013.01)

(58) Field of Classification Search
CPC ............ A61B 18/042; A61B 2018/122; A61B 2018/1213; A61F 7/0085; A61H 2033/141; A61N 1/44
See application file for complete search history.

*Primary Examiner* — Deanna K Hall
(74) *Attorney, Agent, or Firm* — LIANG LEGAL GROUP, PLLC

(57) ABSTRACT

A hot plasma disease treatment system includes a mutually connected control system and at least one power supply system, the control system and the power supply system respectively being connected to and controlling a medium gas modulation system, at least one cooling system, at least one hot plasma generator, at least one plasma processing apparatus, a plasma treatment cabin, a detection feedback system, and a tail gas processing system, the medium gas modulation system being connected to the hot plasma generator, the cooling system being arranged on the hot plasma generator, the hot plasma generator and the plasma processing apparatus being connected, the plasma processing apparatus and the plasma treatment cabin being connected, and the plasma treatment cabin and the tail gas processing system being connected.

18 Claims, 3 Drawing Sheets

HOT PLASMA DISEASE TREATMENT SYSTEM AND METHOD OF USE THEREOF

BACKGROUND OF THE INVENTION

Technical Field

The present invention relates to the field of plasma medical devices, and in particular provides hot plasma disease treatment systemS and methods of use thereof.

Background Art

Plasma is a fourth state aside from solid, liquid, and gas, and 99% of the matter in the universe is in the plasma state. Plasma is usually divided into equilibrium plasma, also called hot plasma (with the electron temperature equal to the heavy particle temperature), and non-equilibrium plasma, also called cold plasma (with the electron temperature greater than 10000 K, which is much higher than the heavy particle temperature close to room temperature).

Application of cold plasma in medical research has been a hot spot for scientists for the past 20 years. Encouraging effects have been achieved in dealing with bacteria and viruses on the skin surface and subcutaneous tumors. However, due to technical limitations, cold plasma has the following disadvantages:
1. The output powers of cold plasma devices are low, and the plasma jets generated are weak for biological treatments;
2. A cold plasma jet has a small flow and a low flow rate, and has a small coverage the surface area for a body. Therefore, cold plasma is mainly used in sterilization, local treatments of wounds, skin surface treatments, etc., and its application scope is narrow. There is no cure for viruses such as systemic viral diseases in a living body and deep (visceral) viruses in a living body.

SUMMARY OF THE PRESENT INVENTION

An objective of the present invention is to provide hot plasma disease treatment systems and methods of use thereof, which can be used not only for sterilization of the surface of a living body and local treatment of wounds, but also for rehabilitation and treatment of diseases such as systemic viral diseases of a living body, diseases of deep viruses such as visceral viruses in a living body, and nervous system degenerative disease.

The present invention may be achieved with following technical solutions, which may comprise a mutually connected control system and at least one power supply system. The control system and the power supply system are, respectively, connected to and control a medium gas modulation system, at least one cooling system, at least one hot plasma generator, at least one plasma processing apparatus, a plasma treatment cabin, a detection feedback system, and a tail gas processing system. The medium gas modulation system is connected to the hot plasma generator, and the cooling system is disposed on the hot plasma generator. The hot plasma generator is connected to the plasma processing apparatus, and the plasma processing apparatus is connected to the plasma treatment cabin. The plasma treatment cabin is connected to the tail gas processing system. The detection feedback system is connected to the hot plasma generator and the plasma treatment cabin. The detection feedback system sends detection data to the control system for calculation.

The plasma processing apparatus comprises a receiving portion 1, a processing portion 2, an output portion 3, a coolant inlet 4, a coolant container 7, and a coolant outlet 5, wherein the receiving portion 1 is connected to the hot plasma generator, the output portion 3 is connected to the plasma treatment cabin, two ends of the processing portion 2 are respectively connected to the receiving portion 1 and the output portion 3, the coolant inlet 4 is disposed on the receiving portion 1, the coolant container 7 is disposed outside the processing portion 2, the coolant outlet 5 is disposed on the output portion 3, and a coolant is used to cool a hot plasma jet within the processing portion 2.

The plasma processing apparatus comprises a receiving portion 1, a processing portion 2, an output portion 3, and a jet regulating wind inlet 6, wherein the receiving portion 1 is connected to the hot plasma generator, the output portion 3 is connected to the plasma treatment cabin, two ends of the processing portion 2 are respectively connected to the receiving portion 1 and the output portion 3, and the jet regulating wind inlet 6 is disposed on the receiving portion 1. Jet regulating wind is used to lower the temperature of a hot plasma jet and to maintain a stable output of hot plasma jets to the plasma treatment cabin.

The plasma processing apparatus comprises a receiving portion 1, a processing portion 2, an output portion 3, a coolant inlet 4, a coolant container 7, a coolant outlet 5, and a jet regulating wind inlet 6, wherein the receiving portion 1 is connected to the hot plasma generator, the output portion 3 is connected to the plasma treatment cabin, two ends of the processing portion 2 are respectively connected to the receiving portion 1 and the output portion 3, the coolant inlet 4 is disposed on the receiving portion 1, the coolant container 7 is disposed outside the processing portion 2, the plasma coolant outlet 5 is disposed on the output portion 3, and the jet regulating wind inlet 6 is disposed on the receiving portion 1.

The processing portion 2 of the plasma processing apparatus has a cross section that is 0.2 times to 2 times the cross section of the anode nozzle of the hot plasma generator.

The plasma processing apparatus has the functions of noise reduction and light shielding, sealing a hot plasma jet in the plasma processing apparatus. It not only effectively reduces the noise of the hot plasma jet, but also allows a therapist to avoid the irradiation by the intense light emitted by the hot plasma.

The plasma processing apparatus further has a collecting function, which prevents the mixing of a hot plasma jet and the outside air, and prevents an effective substance from being dispersed and lost in the environment, thereby preventing the therapeutic effect from being affected.

The shape of the processing portion 2 of the plasma processing apparatus may be straight, curved, spiral, or twisted.

The height and the angle of rotation of the output portion 3 of the plasma processing apparatus may be adjusted manually or automatically by a control unit.

The cross sections of the receiving portion 1, the processing portion 2, the output portion 3, the coolant inlet 4, the coolant outlet 5, and the jet regulating wind inlet 6 of the plasma processing apparatus may be circular, elliptical, or polygonal.

The coolant in the cooling system and the coolant container 7 may be a gas or a liquid.

The medium gas modulation system selects an input type of the medium gas and controls a flow rate of the medium gas.

The medium gas in the medium gas modulation system may be one or more of argon gas, helium gas, nitrogen gas, air, nitrogen dioxide gas, nitrogen monoxide gas, oxygen gas, methane gas, hydrogen gas, ammonia gas, carbon dioxide gas, carbon monoxide gas, alcohol vapor, and water vapor, and one or more of argon gas, helium gas, and nitrogen gas, at a flow rate of 8 L/min to 240 L/min; one or more of air, nitrogen dioxide gas, nitrogen monoxide gas, and oxygen gas, at a flow rate of 15 L/min to 3200 L/min; and one or more of methane gas, hydrogen gas, ammonia gas, carbon dioxide gas, carbon monoxide gas, alcohol vapor, and water vapor, at a flow rate of 0.8 L/min to 18.2 L/min.

The power of the power supply system is 500 W to 1000 kW.

The hot plasma generator may be one or more of a DC plasma generator, an AC plasma generator, a microwave plasma generator, and a high-frequency inductive plasma generator, and has a power of 500 W to 450 kW.

The detection feedback system, by means of the sensors installed in the hot plasma generator and the plasma treatment cabin, and the biometric vital sign monitoring sensor installed in the plasma treatment cabin, detects various data, including real-time physiological data, such as heart rates, blood pressures, and blood oxygen levels of the living body (the subject) to be treated, and parameters of the hot plasma generator and the plasma treatment cabin, such as power, temperature field of the plasma jet, and gas flow, and then sends the acquired data to the control system; the control system performs calculation based on the acquired data, and adjusts the operating conditions of the equipment according to the calculated data, so that the data in the treatment cabin meet the requirements for treating diseases.

The plasma treatment cabin is provided with a biometric breathing apparatus, noise reduction earphones, a biometric vital sign monitoring sensor, and an ambient temperature regulating apparatus. The ambient temperature regulating apparatus is used to regulate the temperature in the plasma treatment cabin.

Disease types to be treated may include:
A. Body surface diseases, such as skin diseases, chronic ulcers, viral infections, and bacterial/fungal infections;
B. In vivo viral diseases, such as hepatitis B, hepatitis C, canine distemper virus disease, and canine parvovirus disease;
C. Tumorous diseases, such as melanoma, liver cancer, lung cancer, and glioma;
D. Immune system diseases, such as rheumatoid arthritis, systemic lupus erythematosus, scleroderma, and ankylosing spondylitis;
E. Nervous system degenerative diseases, such as Parkinson's disease and cerebellar atrophy.

In actual operations, an operator makes adjustments based on different diseases, physical responses of different patients, and real-time parameters of the biometric vital sign monitoring sensor, including the medium gas type, medium gas flow rate, power of the hot plasma generator and that of the plasma processing apparatus, and treatment time and cycle.

A method may comprise the following steps: the power supply system is started, the control system controls the medium gas modulation system to modulate the medium gas and then feeds it into the hot plasma generator, and the modulated medium gas forms a hot plasma jet after arcing by the hot plasma generator; the hot plasma jet is processed by the plasma processing apparatus to form a working gas having a temperature below 70° C., the working gas enters the plasma treatment cabin, and the tail (exhaust) gas from the plasma treatment cabin enters the tail gas processing system for tail/exhaust gas processing; the detection feedback system, by means of the sensors installed in the hot plasma generator and the plasma treatment cabin and the biometric vital sign monitoring sensor installed in the plasma treatment cabin, acquires real-time physiological data, such as heart rates, blood pressures, and blood oxygen levels of the living body to be treated, and parameters of the hot plasma generator and the plasma treatment cabin, such as power, temperature field of the plasma jet, and gas flow, and then sends the acquired data to the control system; the control system performs calculation on the acquired data, and adjusts the operating conditions of the equipment according to the calculated data, so that the data in the treatment cabin meet the requirements for treating diseases.

The present invention, by modulation of hot plasma treatment, can treat various diseases including body surface diseases, in vivo viral diseases, tumorous diseases, immune system diseases, and nervous system degenerative diseases, providing novel treatment systems and methods for the treatments of diseases.

Figure 1:
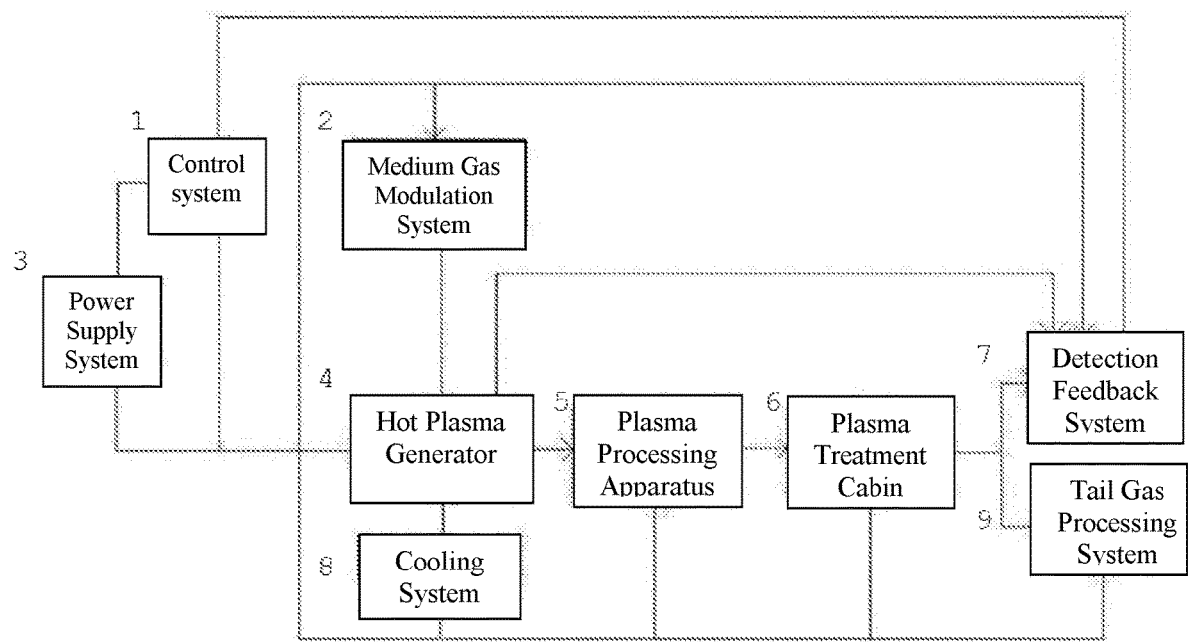
FIG. 1 shows a block diagram illustrating the overall principle of a hot plasma disease treatment system according to embodiments of the present invention.

The reference numerals in the figures are as follows: 1: receiving portion; 2: processing portion; 3: output portion; 4: coolant inlet; 5: coolant outlet; 6: jet regulating wind inlet; 7: coolant container.

DETAILED DESCRIPTION

As shown in FIG. 1, a hot plasma disease treatment system of the invention comprises a control system, a power supply system, a medium gas modulation system, a cooling system, a hot plasma generator, a plasma processing apparatus, a plasma treatment cabin, a detection feedback system, and a tail gas processing system. The control system and the power supply system are mutually connected and control the medium gas modulation system, the cooling system, the hot plasma generator, the plasma processing apparatus, the plasma treatment cabin, the detection feedback system, and the tail gas processing system. The medium gas modulation system is connected to the hot plasma generator; the cooling system is disposed on the hot plasma generator; the hot plasma generator is connected to the plasma processing apparatus; the plasma processing apparatus is connected to the plasma treatment cabin; the plasma treatment cabin is connected to the tail gas processing system; the detection feedback system is connected to the hot plasma generator and the plasma treatment cabin; and the detection feedback system sends detection data to the control system for calculation.

Figure 2:
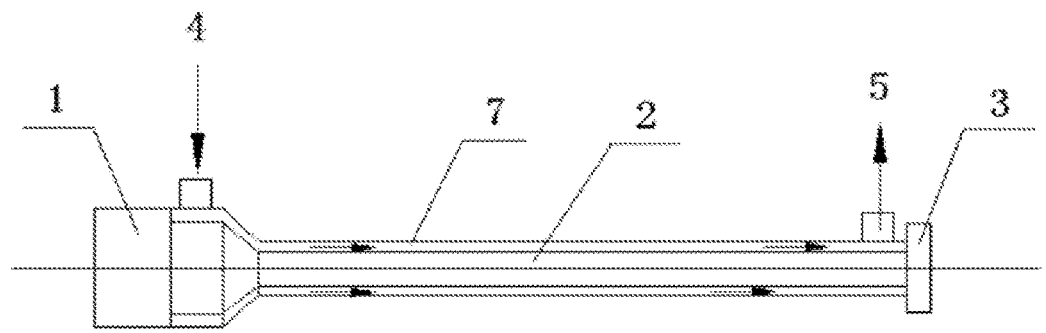
FIG. 2 shows a schematic view of a plasma processing apparatus with a coolant according to embodiments of the present invention.

As shown in FIG. 2, a plasma processing apparatus of the invention may comprise a receiving portion 1, a processing portion 2, an output portion 3, a coolant inlet 4, a coolant container 7, and a coolant outlet 5, wherein the receiving portion 1 is connected to the hot plasma generator, and the output portion 3 is connected to the plasma treatment cabin. Two ends of the processing portion 2 are respectively connected to the receiving portion 1 and the output portion 3. The coolant inlet 4 is disposed on the receiving portion 1, the coolant container 7 is disposed outside the processing portion 2, and the coolant outlet 5 is disposed on the output portion 3.

Figure 3:
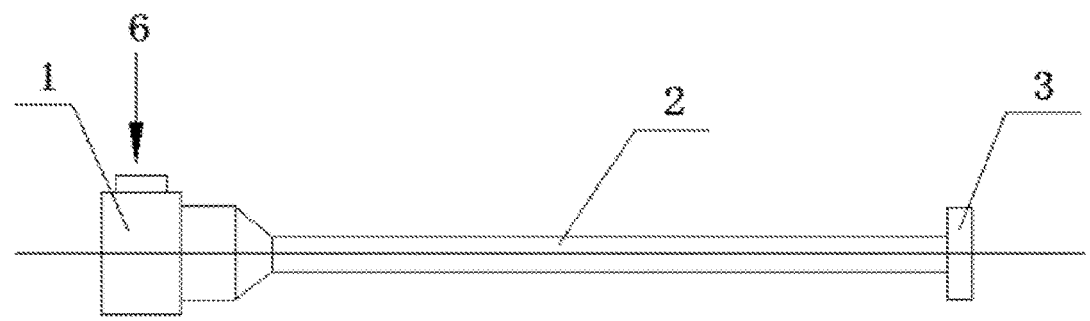
FIG. 3 shows a schematic view of a plasma processing apparatus with jet regulating wind according to embodiments of the present invention.

As shown in FIG. 3, a plasma processing apparatus of the invention may comprise a receiving portion 1, a processing portion 2, an output portion 3, and a jet regulating wind inlet 6, wherein the receiving portion 1 is connected to the hot plasma generator, the output portion 3 is connected to the plasma treatment cabin. Two ends of the processing portion 2 are respectively connected to the receiving portion 1 and the output portion 3, and the jet regulating wind inlet 6 is disposed on the receiving portion 1.

Figure 4:
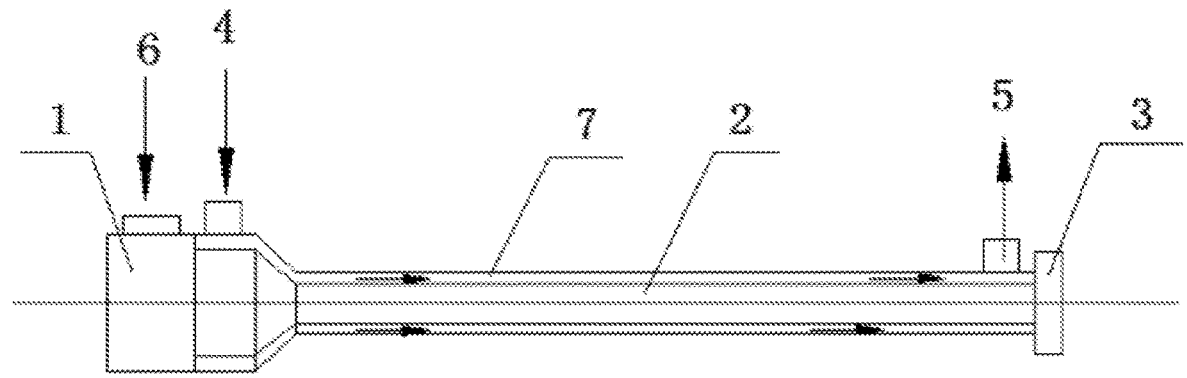
FIG. 4 shows a schematic view of a plasma processing apparatus with a coolant and a jet regulating wind according to embodiments of the present invention.

As shown in FIG. 4, a plasma processing apparatus of the invention may comprise a receiving portion 1, a processing portion 2, an output portion 3, a coolant inlet 4, a coolant container 7, a coolant outlet 5, and a jet regulating wind inlet 6, wherein the receiving portion 1 is connected to the hot plasma generator, the output portion 3 is connected to the plasma treatment cabin. Two ends of the processing portion 2 are respectively connected to the receiving portion 1 and the output portion 3, the coolant inlet 4 is disposed on the receiving portion 1, the coolant container 7 is disposed outside the processing portion 2, the coolant outlet 5 is disposed on the output portion 3, and the jet regulating wind inlet 6 is disposed on the receiving portion 1.

Figure 5:
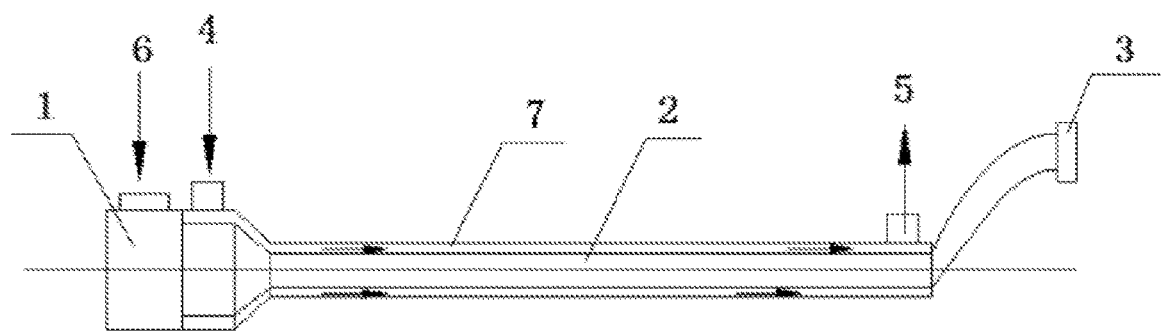
FIG. 5 shows a schematic view of the output portion of the plasma processing apparatus that has an adjustable height and angle of rotation according to embodiments of the present invention.

As shown in FIG. 5, the height and the angle of rotation of the output portion 3 of a plasma processing apparatus may be adjusted manually or automatically by a control unit.

As shown in FIGS. 2 to 5, the processing portion 2 of the plasma processing apparatus may have a cross section that is smaller than the cross section of the anode nozzle of the hot plasma generator.

Figure 6:
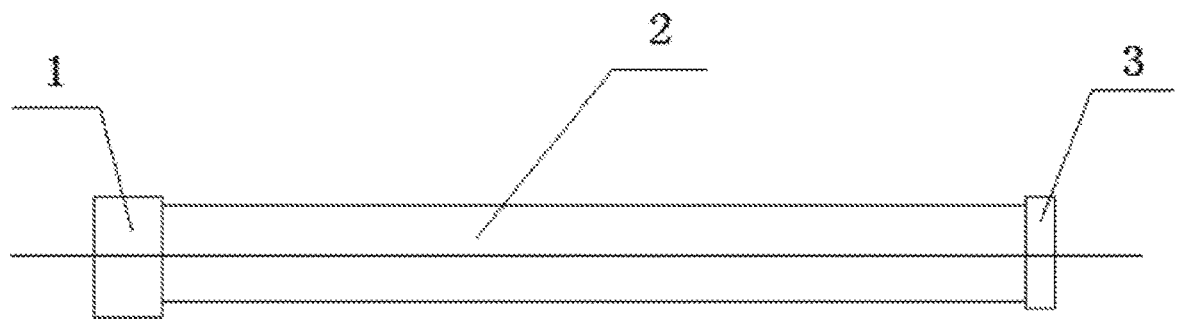
FIG. 6 shows a schematic view illustrating that the cross section of the processing portion of the plasma processing apparatus according to an embodiment of the present invention may be the same as the cross section of the anode nozzle of the hot plasma generator.

As shown in FIG. 6, the processing portion 2 of the plasma processing apparatus may have a cross section the same as the cross section of the anode nozzle of the hot plasma generator.

Figure 7:
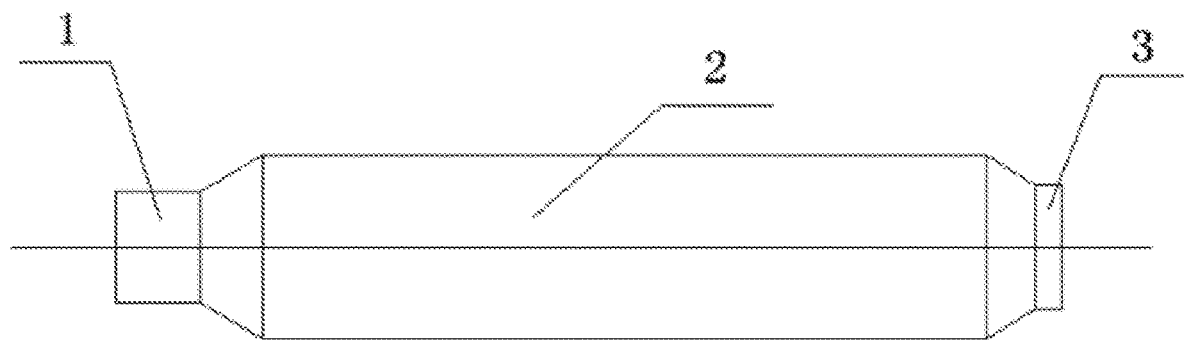
FIG. 7 shows a schematic view illustrating that the cross section of the processing portion of the plasma processing apparatus according to an embodiment of the present invention may be larger than the cross section of the anode nozzle of the hot plasma generator.

As shown in FIG. 7, the processing portion 2 of the plasma processing apparatus may have a cross section that is larger than the cross section of the anode nozzle of the hot plasma generator.

Figure 8:
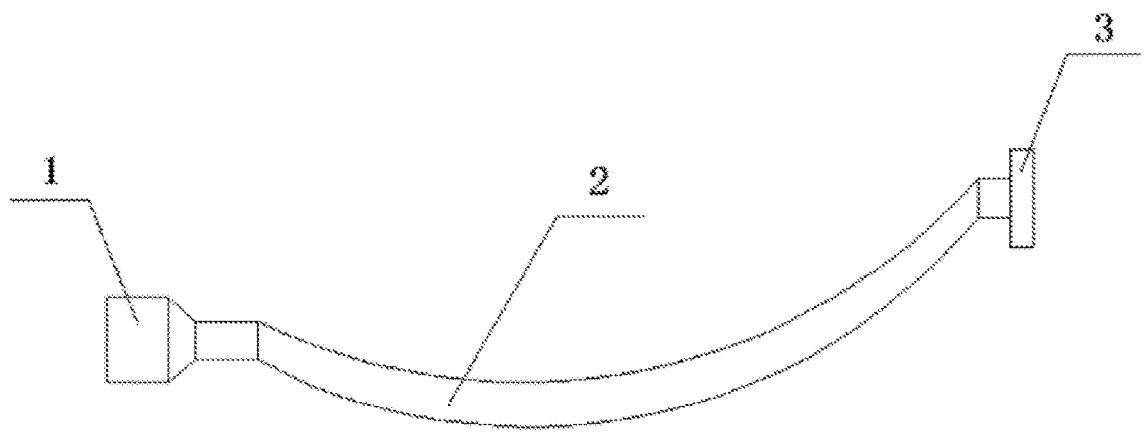
FIG. 8 shows a schematic view illustrating that the processing portion of the plasma processing apparatus according to embodiments of the present invention may be in a curved shape.

As shown in FIG. 8, the processing portion 2 of the plasma processing apparatus may be curved.

The height and the angle of rotation of the output portion 3 of the plasma processing apparatus may be adjusted manually or automatically by a control unit.

The cross sections of the receiving portion 1, the processing portion 2, the output portion 3, the coolant inlet 4, the coolant outlet 5, and the jet regulating wind inlet 6 of the plasma processing apparatus may be circular, elliptical, or polygonal.

The coolant in the cooling system and the coolant container 7 may be a gas or a liquid.

The medium gas modulation system selects an input type of the medium gas and controls a flow rate of the medium gas.

The medium gas in the medium gas modulation system may be one or more of argon gas, helium gas, nitrogen gas, air, nitrogen dioxide gas, nitrogen monoxide gas, oxygen gas, methane gas, hydrogen gas, ammonia gas, carbon dioxide gas, carbon monoxide gas, alcohol vapor, and water vapor, and one or more of argon gas, helium gas, and nitrogen gas, at a flow rate of 8 L/min to 240 L/min; one or more of air, nitrogen dioxide gas, nitrogen monoxide gas, and oxygen gas, at a flow rate of 15 L/min to 3200 L/min; and one or more of methane gas, hydrogen gas, ammonia gas, carbon dioxide gas, carbon monoxide gas, alcohol vapor, and water vapor, at a flow rate of 0.8 L/min to 18.2 L/min.

The power of the power supply system may be 1 kW to 1000 kW.

The hot plasma generator may be one or more DC plasma generators, AC plasma generators, microwave plasma generators, and high-frequency inductive plasma generators of the same model, or a plurality of generators of different models, with a power of 500 W to 450 kW.

The detection feedback system, by means of the sensors installed in the hot plasma generator and the plasma treatment cabin, and the biometric vital sign monitoring sensor installed in the plasma treatment cabin, detects various data, including real-time physiological data, such as heart rates, blood pressures, and blood oxygen levels, of the living body (the subject) to be treated, and parameters of the hot plasma generator and the plasma treatment cabin, such as power, temperature field of the plasma jet, and gas flow, and then sends the acquired data to the control system; the control system calculates the acquired data, and adjusts the operating conditions of the equipment according to the calculated data, so that the data in the treatment cabin meet the requirements for treating diseases.

The plasma treatment cabin is provided with a biometric breathing apparatus, noise reduction earphones, a biometric vital sign monitoring sensor, and an ambient temperature regulating apparatus. The ambient temperature regulating apparatus is used to regulate the temperature in the plasma treatment cabin.

Disease types to be treated may include:
A. Body surface diseases, such as skin diseases, chronic ulcers, viral infections, and bacterial/fungal infections;
B. In vivo viral diseases, such as hepatitis B, hepatitis C, canine distemper virus disease, and canine parvovirus disease;
C. Tumorous diseases, such as melanoma, liver cancer, lung cancer, and glioma;
D. Immune system diseases, such as rheumatoid arthritis, systemic lupus erythematosus, scleroderma, and ankylosing spondylitis;
E. Nervous system degenerative diseases, such as Parkinson's disease and cerebellar atrophy.

In actual operations, an operator makes adjustments based on different diseases, physical responses of different patients, and real-time parameters of the biometric vital sign monitoring sensor, including the medium gas type, medium gas flow rate, power of the hot plasma generator and that of the plasma processing apparatus, and treatment time and cycle.

A hot plasma disease treatment system of the invention works as follows:

A diseased living body (subject) enters the plasma treatment cabin, wears the biometric breathing apparatus, the noise reduction earphones, and the biometric vital sign monitor sensor, has the affected skin exposed, and is ready to receive treatment.

After confirming that the diseased living body is ready, the operator starts the power supply system. The control system controls the medium gas modulation system to modulate the medium gas and then feeds it into the hot plasma generator. The modulated medium gas forms a hot plasma jet after arcing by the hot plasma generator. The hot plasma jet is processed by the plasma processing apparatus to form a working gas having a temperature below 70° C. The working gas enters the plasma treatment cabin and comes into contact with the skin of the living body for disease treatment.

After the treatment, the tail/exhaust gas from the plasma treatment cabin enters the tail gas processing system for tail gas processing. The detection feedback system, by the sensors installed in the hot plasma generator and the plasma treatment cabin and the sensors installed in the plasma treatment cabin, acquires real-time physiological data, such as heart rate, blood pressure, and blood oxygen, of the living body to be treated, and parameters of the hot plasma generator and the plasma treatment cabin, such as power, temperature field of the plasma jet, and gas flow, and then sends the acquired data to the control system; the control system calculates the acquired data, and adjusts the operating conditions of the equipment according to the calculated data, so that the data in the treatment cabin meet the requirements for treating diseases.

What is claimed is:

1. A hot plasma disease treatment system, comprising:
   a control system connected with a power supply system, wherein the control system and the power supply system are respectively connected to and control a medium gas modulation system, at least one cooling system, at least one hot plasma generator, at least one plasma processing apparatus, a plasma treatment cabin, a detection feedback system, and a tail gas processing system;
   wherein the medium gas modulation system is connected to the hot plasma generator,
   wherein the cooling system is disposed on the hot plasma generator,
   wherein the hot plasma generator is connected to the plasma processing apparatus, and the plasma processing apparatus is connected to the plasma treatment cabin,
   wherein the plasma treatment cabin is connected to the tail gas processing system,
   wherein the detection feedback system is connected to the hot plasma generator and the plasma treatment cabin, and
   wherein the detection feedback system is configured to send detection data to the control system for calculation.

2. The hot plasma disease treatment system according to claim 1, wherein the plasma processing apparatus comprises a receiving portion, a processing portion, an output portion, a coolant inlet, a coolant container, and a coolant outlet, wherein the receiving portion is connected to the hot plasma generator, wherein the output portion is connected to the plasma treatment cabin, wherein two ends of the processing portion are respectively connected to the receiving portion and the output portion, wherein the coolant inlet is disposed on the receiving portion, wherein the coolant container is disposed outside the processing portion, and wherein the coolant outlet is disposed on the output portion.

3. The hot plasma disease treatment system according to claim 1, wherein the plasma processing apparatus comprises a receiving portion, a processing portion, an output portion, and a jet regulating wind inlet, wherein the receiving portion is connected to the hot plasma generator, wherein the output portion is connected to the plasma treatment cabin, wherein two ends of the processing portion are respectively connected to the receiving portion and the output portion, and wherein the jet regulating wind inlet is disposed on the receiving portion.

4. The hot plasma disease treatment system according to claim 2, wherein the plasma processing apparatus comprises a receiving portion, a processing portion, an output portion, a coolant inlet, a coolant container, a coolant outlet, and a jet regulating wind inlet, wherein the receiving portion is connected to the hot plasma generator, wherein the output portion is connected to the plasma treatment cabin, wherein two ends of the processing portion are respectively connected to the receiving portion and the output portion, wherein the coolant inlet is disposed on the receiving portion, wherein the coolant container is disposed outside the processing portion, wherein the coolant outlet is disposed on the output portion, and wherein the jet regulating wind inlet is disposed on the receiving portion.

5. The hot plasma disease treatment system according to claim 2, wherein the processing portion of the plasma processing apparatus has a cross section that is 0.2 times to 2 times a cross section of an anode nozzle of the hot plasma generator.

6. The hot plasma disease treatment system according to claim 3, wherein the processing portion of the plasma processing apparatus has a cross section that is 0.2 times to 2 times a cross section of an anode nozzle of the hot plasma generator.

7. The hot plasma disease treatment system according to claim 4, wherein the processing portion of the plasma processing apparatus has a cross section that is 0.2 times to 2 times a cross section of an anode nozzle of the hot plasma generator.

8. The hot plasma disease treatment system according to claim 2, wherein a shape of the processing portion of the plasma processing apparatus is straight, curved, spiral, or twisted.

9. The hot plasma disease treatment system according to claim 1, wherein a height and an angle of rotation of the output portion of the plasma processing apparatus are adjusted manually or automatically by a control unit.

10. The hot plasma disease treatment system according to claim 2, wherein cross sections of the receiving portion, the processing portion, the output portion, the coolant inlet, the coolant outlet, and the jet regulating wind inlet of the plasma processing apparatus are circular, elliptical, or polygonal.

11. The hot plasma disease treatment system according to claim 2, wherein a coolant in the cooling system and the coolant container is a gas or a liquid.

12. The hot plasma disease treatment system according to claim 1, wherein the medium gas modulation system selects an input type of a medium gas and controls a flow rate of the medium gas.

13. The hot plasma disease treatment system according to claim 1, wherein a medium gas in the medium gas modulation system is one or more of argon gas, helium gas, nitrogen gas, air, nitrogen dioxide gas, nitrogen monoxide gas, oxygen gas, methane gas, hydrogen gas, ammonia gas, carbon dioxide gas, carbon monoxide gas, alcohol vapor, and water vapor, or one or more of argon gas, helium gas, and nitrogen gas, at a flow rate of 8 L/min to 240 L/min; or one or more of air, nitrogen dioxide gas, nitrogen monoxide gas, and oxygen gas, at a flow rate of 15 L/min to 3200 L/min; or one or more of methane gas, hydrogen gas, ammonia gas, carbon dioxide gas, carbon monoxide gas, alcohol vapor, and water vapor, at a flow rate of 0.8 L/min to 18.2 L/min.

14. The hot plasma disease treatment system according to claim 1, wherein the hot plasma generator is a DC plasma generator an AC plasma generator, a microwave plasma generator, or a high-frequency inductive plasma generator.

15. The hot plasma disease treatment system according to claim 1, wherein the detection feedback system, by means of sensors installed in the hot plasma generator and the plasma treatment cabin, and a biometric vital sign monitoring sensor installed in the plasma treatment cabin, detects data and then sends the data to the control system for calculation.

16. The hot plasma disease treatment system according to claim 1, wherein the plasma treatment cabin is provided with a biometric breathing apparatus, noise reduction earphones, a biometric vital sign monitoring sensor, and an ambient temperature regulating apparatus.

17. The hot plasma disease treatment system according to claim 1, wherein the system is configured to treat a disease selected from the group consisting of a body surface disease, an in vivo viral disease, a tumorous disease, an immune disease, and a nervous system disease.

18. A method of using the hot plasma disease treatment system according to claim 1, wherein the method comprises:
   starting the power supply system;
   using the control system, controlling the medium gas modulation system to modulate a medium gas and then feeding the modulated medium gas into the hot plasma generator;
   forming a hot plasma jet from the modulated medium gas after arcing by the hot plasma generator;
   processing the hot plasma jet by the plasma processing apparatus to form a working gas having a temperature below 70° C.;
   introducing the working gas into the plasma treatment cabin;
   passing a tail gas from the plasma treatment cabin into the tail gas processing system for tail gas processing;
   using the detection feedback system and sensors installed in the hot plasma generator and the plasma treatment cabin, acquiring real-time physiological data of a subject to be treated and parameters of the hot plasma generator and the plasma treatment cabin, and then sending the acquired data to the control system; and
   using the control system, performing calculation on the acquired data, and adjusting operating conditions of the hot plasma disease treatment system.

\* \* \* \* \*